United States Patent
Zhang

(10) Patent No.: US 8,860,438 B2
(45) Date of Patent: Oct. 14, 2014

(54) ELECTRICAL DOUBLE LAYER CAPACITIVE DEVICES AND METHODS OF USING SAME FOR SEQUENCING POLYMERS AND DETECTING ANALYTES

(75) Inventor: Guigen Zhang, Clemson, SC (US)

(73) Assignee: Clemson University Research Foundation, Clemson, SC (US)

( * ) Notice: Subject to any disclaimer, the term of this patent is extended or adjusted under 35 U.S.C. 154(b) by 549 days.

(21) Appl. No.: 12/777,377

(22) Filed: May 11, 2010

(65) Prior Publication Data
US 2010/0289505 A1    Nov. 18, 2010

Related U.S. Application Data

(60) Provisional application No. 61/177,011, filed on May 11, 2009.

(51) Int. Cl.
*G01R 27/26*    (2006.01)

(52) U.S. Cl.
USPC ............................ 324/663; 324/658; 324/661

(58) Field of Classification Search
CPC .................. C12Q 1/6869; G01N 33/48721
USPC ........................................................ 324/663
See application file for complete search history.

(56) References Cited

U.S. PATENT DOCUMENTS

| | | | |
|---|---|---|---|
| 6,905,586 B2 * | 6/2005 | Lee et al. | 204/600 |
| 7,867,716 B2 * | 1/2011 | Kang et al. | 435/7.1 |
| 8,038,885 B2 * | 10/2011 | Schmidt et al. | 210/639 |
| 8,132,457 B2 * | 3/2012 | Haji-Sheikh et al. | 73/335.04 |
| 2005/0127035 A1 * | 6/2005 | Ling | 216/56 |
| 2006/0029634 A1 * | 2/2006 | Berg et al. | 424/422 |
| 2009/0105427 A1 * | 4/2009 | Thayumanavan et al. | 525/403 |
| 2009/0243584 A1 | 10/2009 | Zhang et al. | |
| 2009/0297913 A1 | 12/2009 | Zhang et al. | |
| 2010/0038243 A1 * | 2/2010 | White et al. | 204/416 |
| 2010/0066346 A1 | 3/2010 | Zhang et al. | |
| 2010/0084276 A1 * | 4/2010 | Lindsay | 205/93 |
| 2011/0053794 A1 * | 3/2011 | Zhang | 506/9 |
| 2011/0192723 A1 * | 8/2011 | Chen et al. | 204/451 |
| 2014/0011691 A1 * | 1/2014 | Sierks et al. | 506/9 |

OTHER PUBLICATIONS

Nanopore, from Wikipedia, Sep. 26, 2012, p. 1.*
Compare Anything—Bacteria vs Virus, Sep. 26, 2012, p. 1-2.*
He et al., Dynamic diffuse double-layer model fo the electrochemistry of nanometer-sized electrodes, J. Phys. Chem. B, 2006, 110, 3262-3270.*
Laikhtman, Tunneling time and effective capacitance for single electron tunneling, Physics Letters A, V. 139, Issues 5-6, 1989, p. 257-260.*
Branton et al. "The potential and challenges of nanopore sequencing", *Nature Biotechnology* 26(10):1146-1153 (2008).

(Continued)

*Primary Examiner* — Thomas F Valone
(74) *Attorney, Agent, or Firm* — Myers Bigel Sibley & Sajovec, P.A.

(57) ABSTRACT

Provided according to some embodiments of the present invention are electrical double layer (EDL) capacitive devices that include an insulating substrate defining a nanopore therethrough; a nanopore electrode exposed in a portion of the nanopore; and an electrolyte in contact with the nanopore electrode. Also provided are methods of using EDL capacitive devices according to embodiments of the invention to sequence polynucleotides or other polymers and/or to detect analytes.

25 Claims, 11 Drawing Sheets

(56) References Cited

OTHER PUBLICATIONS

Coombs "The sequencing shakeup", *Nature Biotechnology* 26(10):1109-1112 (2008).

Grahame "The Electrical Double Layer and the Theory of Electrocapillarity", *Chem. Rev.* 41:441-501 (1947).

He et al. "Identification of DNA Basepairing via Tunnel-Current Decay", *Nano Letters* 7(12):3854-3858 (2007).

Heng et al. "Beyond the Gene Chip", *Bell Labs Tech. Journal* 10(3):5-22 (2005).

Ho et al. "Electrolytic transport through a synthetic nanometer-diameter pore", *PNAS* 102(30):10445-10450 (2005).

Kolb "Electrochemical Surface Science", *Angew. Chem. Int. Ed.* 40:1162-1181 (2001).

Lagerqvist et al. "Influence of the Environment and Probes on Rapid DNA Sequencing via Transverse Electronic Transport", *Biophysical Journal* 93:2384-2390 (2007).

Parry et al. "In Situ Fourier Transform Infrared Spectroelectrochemical Study of Bisulfate and Sulfate Adsorption on Gold, with and without the Underpotential Deposition of Copper", *Langmuir* 9:1878-1887 (1993).

Singhal et al. "Ultrasensitive Voltammetric Detection of Underivatized Oligonucleotides and DNA", *Anal. Chem.* 69:4828-4832 (1997).

Yang et al. "Simulating the structure and effect of the electrical double layer at nanometer electrodes", *Nanotechnology* 18:1-9 (2007).

Yang et al. "The effect of an electrical double layer on the voltammetric performance of nanoscale interdigitated electrodes: a simulation study", *Nanotechnology* 19:1-8 (2008).

Anandan et al. "Role of reaction kinetics and mass transport in glucose sensing with nanopillar array electrodes", *Journal of Biological Engineering*:1-10 (Oct. 10, 2007).

Anandan et al. "Nanopillar array structures for enhancing biosensing performance", *Int. J. Nanomedicine* 1(1):73-79 (2006).

Lee et al. "Hot Spots in Silver Nanowire Bundles for Surface-Enhanced Raman Spectroscopy", *J. Am. Chem. Soc.* 128:2200-2201 (2006).

Lin et al. "Nanopillar Subtrate for SERS", 7$^{th}$ International Conference on Miniaturized Chemical and Biochemical Analysis Systems 705-708 (Oct. 5-9, 2003).

Masuda et al. "Ordered Metal Nanohole Arrays Made by a Two-Step Replication of Honeycomb Structures of Anodic Alumina", *Science* 268:1466-1468 (1995).

Masuda et al. "Self-repair of ordered pattern of nanometer dimensions based on self-compensation properties of anodic porous alumina", *Applied Physics Letters* 78(6):826-828 (2001).

Moustafa et al. "Electrodeposition of Al in 1-Butyl-1-methylpyrrolidinium Bis(trifluoromethylsulfonyl)amide and 1-Ethyl-3-methylimidazolium Bis(trifluoromethylsulfonyl)amide Ionic Liquids: In Situ STM and EQCM Studies", *J. Phys. Chem. B*. 111:4693-4704 (2007).

Rao et al. "Fast Fourier Transform Analysis of Pore Pattern in Anodized Alumina Formed at Various Conditions", *J. Nanosci. Nanotechnol.* 5(12):2070-2075 (2005).

U.S. Appl. No. 12/869,504, filed Aug. 26, 2010, Zhang.

* cited by examiner

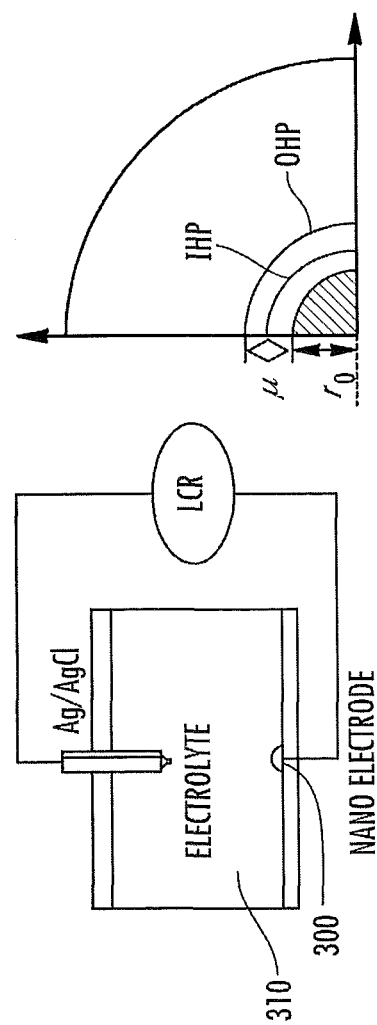
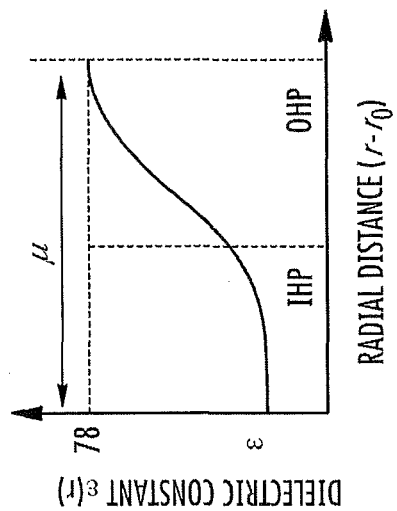
FIG. 3A
FIG. 3B
FIG. 3C

ELECTRICAL DOUBLE LAYER CAPACITIVE DEVICES AND METHODS OF USING SAME FOR SEQUENCING POLYMERS AND DETECTING ANALYTES

CROSS-REFERENCE TO RELATED APPLICATIONS

This application claims priority from U.S. Provisional Application Ser. No. 61/177,011, filed May 11, 2009, the disclosure of which is hereby incorporated by reference herein in its entirety.

FIELD OF THE INVENTION

The present invention relates to devices for sequencing polymers, including polynucleotides, and methods of using the same. The present invention also relates to devices for detecting analytes and methods of using the same.

BACKGROUND OF THE INVENTION

In 2003, an initial draft of the first human genome sequence was completed at a cost of approximately $300 million, excluding the expenses for technological infrastructure. This large expenditure has stimulated competition for a more cost effective method of sequencing polynucleotides. Some of the proposed methods for achieving low cost polynucleotide sequencing utilize wet chemistry-based PCR, synthesis, or ligation methods. However, these methods may face challenges including short reads, PCR-related cost and an undesirable level of errors. Another proposed method uses nano-edge arrays to detect the vibration of individual nucleobases excited by tunneling electrons. However, this method may face challenges related to the uncertainty of electron tunneling in solutions.

A nanopore device provides a highly confined space through which single stranded polynucleotides can pass while individual bases are interrogated consecutively at high throughput without amplification or labeling. One compelling advantage of nanopore sequencing is the prospect of using unamplified genomic DNA, obviating the need for fluorescent reagents, as well as cloning and amplification steps, and eliminating the need for polymerases and ligases during readout. See, Branton et al., *Nature Biotech* 26, 1146 (2008). Thus, the costs of nanopore-based sequencing methods are projected to be far lower than the approaches used today. However, regardless of how promising the nanopore technology may be, several key technological challenges must be addressed before nanopore sequencing can be brought to the market place.

There are two general types of nanopores: natural biopores (e.g., α-hemolysin), and man-made solid-state pores, such those in metal-oxide-semiconductor (MOS) devices. To date, several different modes have been explored to use nanopores to sequence DNA. One technique involves measuring ionic current blockades as single stranded DNA is driven through a nanopore, either a biopore or a solid-state pore. Thus far, however, none of the nanopores studied appears to have the correct geometry to detect one nucleotide at a time while the polymer is translocating through the pore.

An alternative approach has been to measure transverse tunneling currents or capacitance as single stranded DNA is driven through a solid-state nanopore. It has been proposed that tunneling currents through nucleobases may be able to distinguish among the four nucleobases. Currently, two different approaches are typically used to measure such transverse tunneling currents. The first approach is to measure the tunneling current between two metal electrodes passing through a nucleobase of a translocating single stranded DNA. See Di Ventra et al., *Biophys J,* 93, 10, 2384 (2007). The advantage of this approach is that it aims to resolve information regarding a single nucleobase. However, this approach also has challenges. Chiefly, optimal voltage bias and solution conditions must be determined and maintained to provide unambiguous nucleobase identification in solution. Furthermore, the device must assure that each base will assume a reproducible orientation and position on the collector probe while it is being interrogated because tunneling currents are exponentially sensitive to atomic scale changes of orientations and distances.

The second approach has been to form base-specific hydrogen bonds between chemically-modified metal electrodes and the nucleobases. See Lindsay et al., *Nano Lett,* 7, 12, 3854 (2007). A nanopore device having a pair of electrodes functionalized with probes, with one probe able to couple to the nucleotide's phosphate moiety while another probe couples with the nucleobases, has been used in a 'sequence by recognition' scheme to identify the nucleobases. Major challenges of this approach include the need to fit a set of five probes (one for the backbone and four for the bases) at the tip of each nano electrode, and the synchronization of the formation and cleavage of the matching hydrogen bonds during DNA translocation.

Nanopore DNA sequencing based on an MOS capacitor has also been attempted. See Timp et al., *Bell Labs Tech J,* 10, 3, 5 (2005). One advantage of a capacitor-based nanopore device is that it does not have the problems associated with electron tunneling. As single stranded DNA translocates through a nanopore consisting of a parallel-plate MOS capacitor, variation of the electrostatic potential in the pore polarizes the capacitor, resulting in voltage fluctuations on the two silicon plates. In an early trial of this approach, a voltage signal associated with DNA translocation was detected, but it was not possible to distinguish between nucleotides. The pore channel of a length about 40 nm can accommodate a segment of single stranded DNA with about 100 nucleobases, suggesting that the measured results were due to multiple nucleobases. The relatively long span of the MOS capacitor in such a nanopore channel is inherent in the complex nature of an MOS device.

As such, there remains a need in the art for improved nanopore-based sequencing methods. There also remains a need in the art for improved devices and methods for the sequencing of other polymers. Additionally, there remains a need in the art for improved devices and methods for the detection of analytes, particularly biological analytes.

SUMMARY OF THE INVENTION

Provided according to some embodiments of the present invention are electrical double layer (EDL) capacitive devices that include an insulating substrate defining a nanopore therethrough; a nanopore electrode exposed in a portion of the nanopore; and an electrolyte in contact with the nanopore electrode. In particular embodiments, the nanopore electrode defines a conductive ring exposed around an inner surface of the nanopore. In some embodiments, the conductive ring may have a thickness in a range of about 1 angstrom (Å) to about 100 nm, and in some embodiments, the conductive ring may have a width in a range of about 0.5 nm to about 100 μm.

According to some embodiments of the invention, the insulating substrate includes a first insulating layer, the nanopore electrode includes a conductive layer on the first insulating layer, and the EDL capacitive device further includes a second insulating layer on the conductive layer so that the conductive layer is between the first and second insulating layers. The nanopore extends through the first and second insulating layers and through the conductive layer so that portions of the conductive layer are exposed in the nanopore between the first and second insulating layers. In some embodiments, a width of a portion of the nanopore through the first insulating layer is greater than a width of a portion of the nanopore through the nanopore electrode, and a width of a portion of the nanopore through the second insulating layer is greater than a width of the portion of the nanopore through the nanopore electrode.

According to some embodiments of the invention, the first and second insulating layers include at least one of silicon dioxide, silicon nitride, $TiO_2$, $Al_2O_3$, $ZrO_2$, $Ta_2O_5$, AlN, TiN, GaN, GaAs and polyxylylene polymers. Furthermore, in some embodiments of the invention, the conductive layer includes at least one of platinum, gold, titanium, copper, carbon, indium tin oxide and a conductive polymer. Additionally, in some embodiments, the electrolyte includes at least one of potassium chloride (KCl), sodium chloride (NaCl) and phosphate buffered saline (PBS).

According to some embodiments of the invention, the EDL capacitive device also includes a reference electrode in electrical contact with the electrolyte; and a meter electrically coupled between the nanopore electrode and the reference electrode, wherein the meter is configured to measure capacitances between the nanopore electrode and the reference electrode. In some embodiments, the meter is further configured to correlate different measured capacitances with the different monomers of a polymer, such as the nucleotides of a polynucleotide. Furthermore, in some embodiments, the EDL capacitive device further includes a driver circuit configured to generate a biasing potential across the nanopore of the EDL capacitive device to induce an analyte, such as a polynucleotide, to translocate through the nanopore.

Provided according to some embodiments of the invention are methods of determining the nucleotide sequence of a polynucleotide. Such methods include measuring capacitances between a nanoelectrode and an electrolyte in contact with the nanoelectrode as the polynucleotide translocates through the nanopore; and correlating the measured capacitances with nucleotides of the polynucleotide. In some embodiments, one nucleotide of the polynucleotide translocates at the surface of the nanoelectrode at a particular time. In particular embodiments, methods of determining a nucleotide sequence of a polynucleotide include (i) inducing the polynucleotide to translocate through a nanopore of an EDL capacitive device according to an embodiment of the invention; (ii) measuring capacitances between the nanopore electrode and the reference electrode of the EDL capacitive device as the polynucleotide translocates through the nanopore; and (iii) correlating the measured capacitances as the polynucleotide translocates through the nanopore with the nucleotides of the polynucleotide.

Also provided according to some embodiments of the invention are methods of determining a monomer sequence of a polymer that include measuring capacitances between a nanopore electrode and an electrolyte in contact with the nanopore electrode as the polymer translocates a portion of the electrolyte at a surface of the nanopore electrode; and correlating the measured capacitances with monomers of the polymer. In some embodiments, such methods include determining a monomer sequence of a polymer that include (i) inducing the polymer to translocate through a nanopore of an EDL capacitive device that includes (a) an insulating substrate defining the nanopore therethrough; (b) a nanopore electrode exposed in a portion of the nanopore; (c) an electrolyte in contact with the nanopore electrode; and (d) a reference electrode in electrical contact with the nanopore electrode; (ii) measuring capacitances between the nanopore electrode and the reference electrode as the polymer translocates through the nanopore; and (iii) correlating the measured capacitances as the polymer translocates through the nanopore with monomers of the polymer.

In some embodiments of the invention, provided are electrical double layer (EDL) capacitive devices that include an insulating substrate defining a nanopore therethrough; a nanopore electrode exposed in a portion of the nanopore; an electrolyte in contact with the nanopore electrode; a reference electrode in electrical contact with the electrolyte; and a meter electrically coupled between the nanopore electrode and the reference electrode, wherein the meter is configured to measure capacitances between the nanopore electrode and the reference electrode, and wherein the meter is further configured to correlate different measured capacitances with the identity and/or property of an analyte.

Also provided herein are methods of determining the presence and/or a property of an analyte that include (i) inducing the analyte to translocate through a nanopore of an EDL capacitive device that comprises (a) an insulating substrate defining the nanopore therethrough; (b) a nanopore electrode exposed in a portion of the nanopore; (c) an electrolyte in contact with the nanopore electrode; and (d) a reference electrode in electrical contact with the nanopore electrode; (ii) measuring capacitances between the nanopore electrode and the reference electrode as the analyte translocates through the nanopore; and (iii) correlating the measured capacitances as the analyte translocates through the nanopore with the identity and/or property of the analyte.

Furthermore, provided according to some embodiments of the invention are methods of determining the presence and/or a property of an analyte that include measuring capacitances between a nanopore electrode and an electrolyte in contact with the nanopore electrode as the analyte translocates a portion of the electrolyte at a surface of the nanopore electrode; and correlating the measured capacitances with the identity and/or property of the analyte.

In some embodiments, the analyte includes a virus, cell and/or a bacteria.

BRIEF DESCRIPTION OF THE DRAWINGS

The accompanying drawings, which are included to provide a further understanding of the invention and are incorporated in and constitute a part of this application, illustrate certain embodiment(s) of the invention.

FIG. 3A illlustrates the electrochemical model used in a simulation for calculating properties related to the EDL capacitance of a nanoelectrode.

FIG. 3B illustrates a 2D axisymmetric geometric model depicting a spherical nanometer electrode surrounded by an EDL structure in an electrolytic solution. The shaded quarter-circle represents the electrode; IHP=inner Helmholtz plane; and OHP=outer Helmholtz plane.

FIG. 3C is a diagram of a function depicting the dielectric constant of the compact layer of the EDL.

FIG. 4A provides the curve for a compact layer thickness (CLT)=0.66 nm and a dielectric constant ($\in$)=6. FIG. 4B provides the curve for a CLT=0.44 nm and $\in$=6.

DETAILED DESCRIPTION OF EMBODIMENTS OF THE INVENTION

Figure 1A:
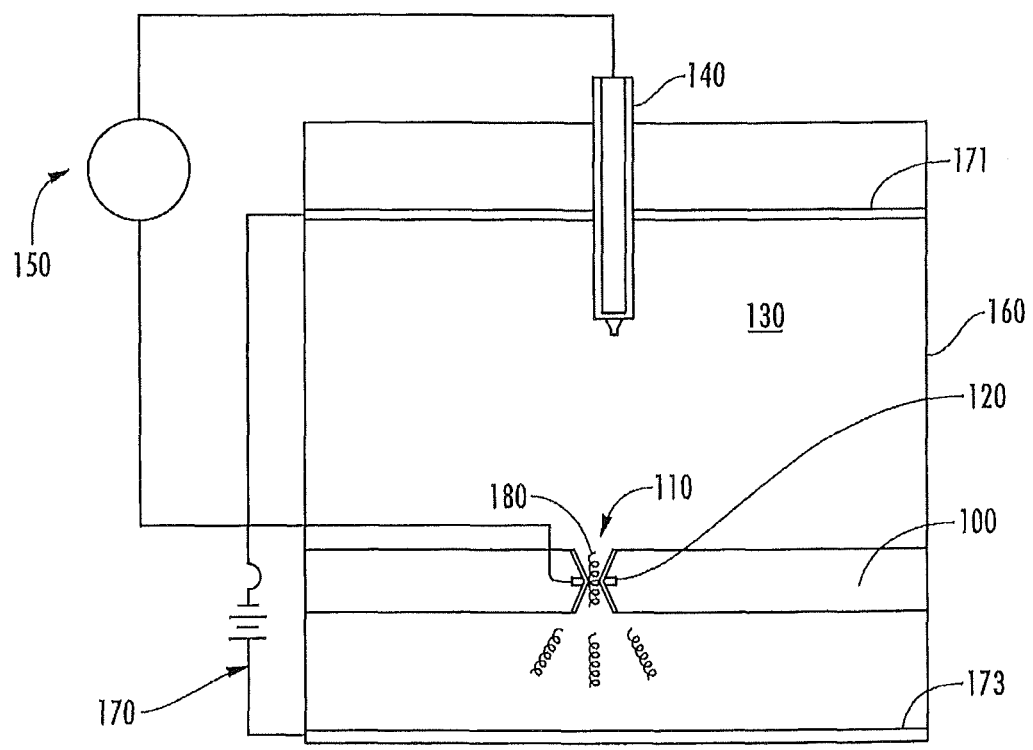
FIG. 1A illustrates a cross sectional view of an EDL capacitive device according to some embodiments of the invention.

Embodiments of the present invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present invention. As used herein, the term "and/or" includes any and all combinations of one or more of the associated listed items.

It will be understood that when an element such as a layer, region or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (i.e., "between" versus "directly between", "adjacent" versus "directly adjacent", etc.).

Relative terms such as "below" or "above" or "upper" or "lower" or "horizontal" or "vertical" may be used herein to describe a relationship of one element, layer or region to another element, layer or region as illustrated in the figures. It will be understood that these terms are intended to encompass different orientations of the device in addition to the orientation depicted in the figures.

Embodiments of the invention are described herein with reference to cross-section illustrations that are schematic illustrations of idealized embodiments (and intermediate structures) of the invention. The dimensions of layers and regions in the drawings may be exaggerated for clarity. Additionally, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing. Thus, the regions illustrated in the figures are schematic in nature and their shapes are not intended to illustrate the actual shape of a region of a device and are not intended to limit the scope of the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms used herein should be interpreted as having a meaning that is consistent with their meaning in the context of this disclosure and the relevant art and will not be interpreted in an idealized or overly formal sense unless expressly so defined herein.

Referring to FIG. 1, provided according to some embodiments of the invention are electrical double layer (EDL) capacitive devices that include an insulating substrate 100 defining a nanopore 110 therethrough; a nanopore electrode 120 exposed in a portion of the nanopore 110; and an electrolyte 130 in contact with the nanopore electrode 120. The width of a particular nanopore may vary as it traverses through the device. For example, the nanopore 110 may become narrower at the location of the nanopore electrode 120. In some embodiments, the nanopore 110 has a width in a range of about 0.5 nm to about 100 µm at the location of the nanopore electrode 120. In particular embodiments, the nanopore 110 has a width in a range of about 0.5 to about 2.5 nm at the location of the nanopore electrode 120. Such devices may be useful, for example, for sequencing polymers such as polynucleotides. In other embodiments, the nanopore 110 has a width in a range of about 10 to about 500 nm at the location of the nanopore electrode 120. Such devices may be useful, for example, for detecting biological analytes such as viruses. Furthermore, in other embodiments, the nanopore 110 has a width in a range of about 0.5 to about 100 µm at the location of the nanopore electrode 120. Such devices may be useful, for example, for detecting biological analytes such as bacteria and cells.

According to some embodiments of the invention, the EDL capacitive device further includes a reference electrode 140 in electrical contact with the electrolyte 130; and a meter 150 electrically coupled between the nanopore electrode 120 and the reference electrode 140. The term "reference electrode" is used to refer to one or more electrodes that provide a reference (e.g. a particular reference voltage) for measurements recorded from the nanopore electrode. Examples of reference electrodes include a standard hydrogen electrode (SHE), an Ag/AgCl reference electrode, a saturated calomel electrode (SCE), and/or a Cu/Cu(II) reference electrode. In some embodiments, the EDL capacitive device may include a container 160 which may house at least some of the other elements of the EDL capacitive devices described herein.

The meter 150 may be configured to measure capacitances between the nanopore electrode 120 and the reference electrode 140. The meter 150 may also be configured to correlate different measured capacitances with the identity or property of an analyte. For example, as shown in FIG. 1, the meter 150 may be configured to correlate different measured capacitance with different nucleotides of a polynucleotide 180. Thus, the term "meter" is meant to encompass one or more devices such as a voltmeter, multi-meter or other capacitance measurement equipment, as well as other electronic equipment used to obtain, process or analyze data obtained from the capacitance measurements. The meter 150, for example, may be configured to apply an AC electrical signal between the nanopore electrode 120 and the reference electrode 140, and to use the applied AC electrical signal to determine a capacitance between the nanopore electrode 120 and the reference electrode 140.

In some embodiments of the invention, the EDL capacitive device further includes a driver circuit 170 configured to generate a biasing potential between biasing electrodes 171 and 173 of the EDL capacitive device to induce an analyte, such as a polynucleotide 180, to translocate through the nanopore 110. Driver circuit 170 may thus generate a biasing potential that induces negatively charged analytes, such as polynucleotides 180, to translocate the nanopore 110.

The insulating substrate 100 of the EDL capacitive device may include any suitable insulating material or combination of insulating materials. Examples of insulating materials include silicon dioxide, silicon nitride, $TiO_2$, $Al_2O_3$, $ZrO_2$, $Ta_2O_5$, AlN, TiN, GaN, GaAs and polyxylylene polymers. The nanopore electrode 120 of the EDL capacitive device may include any suitable conductive material or combination of conductive materials. Examples of conductive materials include platinum, gold, titanium, copper, carbon, indium tin oxide and conductive polymers. The electrolyte 130 of the EDL capacitive device may include any suitable electrolyte or combination of electrolytes. Examples of electrolytes include aqueous solutions of KCl, NaCl and phosphate buffered saline (PBS). In some embodiments, the molarity of the electrolyte is 0.001 M to 2 M, and in some embodiments, the pH is in a range of 7 and 7.4.

Figure 2A:
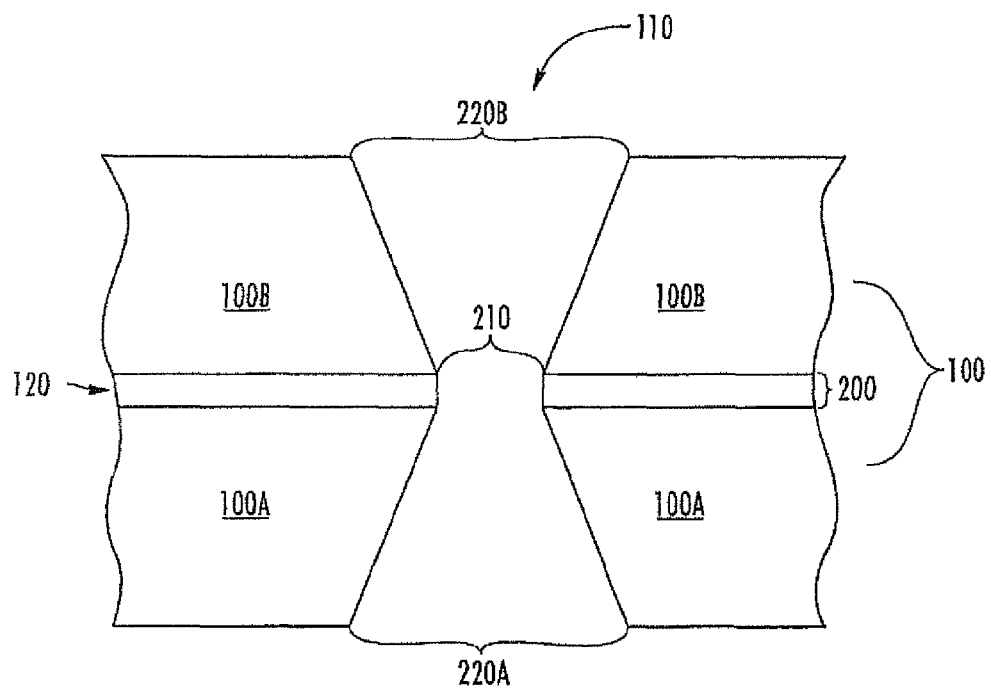
FIG. 2A illustrates a cross-sectional view of a nanopore of an EDL capacitive device according to some embodiments of the invention.
Figure 2B:
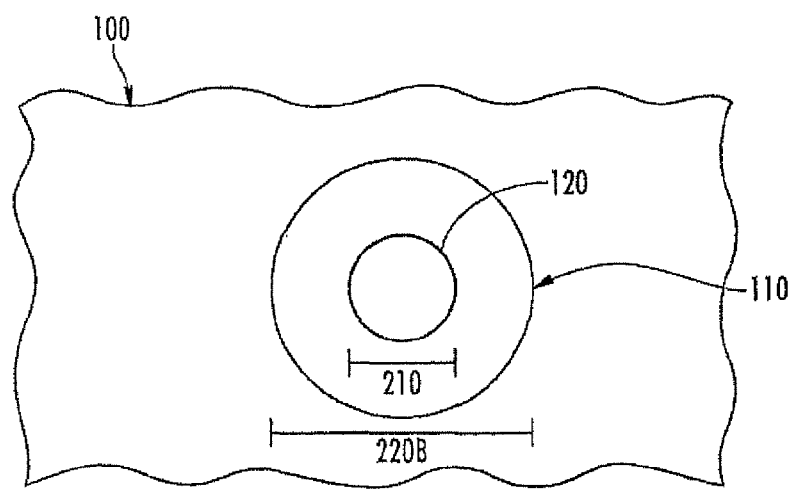
FIG. 2B illustrates a plan view of the EDL capacitive device of FIG. 2A.

The elements of the EDL capacitive device may be present in many different configurations. However, a cross sectional view and a respective plan view of a portion of an insulating substrate 100, nanopore 110 and nanopore electrode 120, according to some embodiments of the invention, is shown in FIGS. 2A and 2B. In some embodiments, the nanopore electrode 120 is formed from a conductive layer within the insulating substrate 100, and the nanopore electrode 120 defines a conductive ring exposed around an inner surface of the nanopore 110. The insulating substrate 100 may include a first insulating layer 100A and a second insulating layer 100B. The conductive layer may be on the first insulating layer 100A and the second insulating layer 100B may be on the conductive layer so that the conductive layer is between the first insulating layer 100A and second insulating layer 100B. A nanopore 110 may extend through the first insulating layer 100A and the second insulating layer 100B and through the conductive layer so that portions of the conductive layer are exposed in the nanopore 110 between the first insulating layer 100A and the second insulating layer 100B, such that a conductive ring 120B is exposed around an inner surface of the nanopore 110. In some embodiments, the conductive ring has a thickness 200 in a range of about 1 Angstrom ($Å$) and about 100 nm. Additionally, in more particular embodiments, the conductive ring has a thickness 200 in a range of about 1 Angstrom (Å) to about 1.0 nm. Such embodiments may be useful for sequencing polymers such as polynucleotides. In particular embodiments, the conductive ring has a thickness 200 in a range of about 5 to about 10 nm. Such embodiments may be useful for detecting biological analytes such as viruses. Furthermore, in particular embodiments, the conductive ring has a thickness 200 in a range of about 5.0 to about 100 nm. Such embodiments may be useful for detecting biological analytes such as cells and bacteria.

The width 220 of a portion of the nanopore 110 through the first insulating layer 100A may be greater than a width 210 of a portion of the nanopore 110 through the conductive ring, and a width 220 of a portion of the nanopore 110 through the second insulating layer 100B may be greater than a width 210 of the portion of the nanopore 110 through the conductive ring. In some embodiments, the width 220 of a portion of the nanopore through the first insulating layer 100A and/or the second insulating layer 100B is in a range of 5 nm to 1 mm. In some embodiments, the width 220 of a portion of the nanopore through the first insulating layer 100A and/or the second insulating layer 100B is in a range of 10 to 50 nm. Such embodiments may be useful for, for example, in devices for sequencing polynucleotides and other polymers. Furthermore, in some embodiments, the width 220 of a portion of the nanopore through the first insulating layer 100A and/or the second insulating layer 100B is in a range of 100 nm to 5 μm. Such embodiments may be useful for, for example, in devices for detecting analytes such as viruses. Additionally, in some embodiments, the width 220 of a portion of the nanopore through the first insulating layer 100A and/or the second insulating layer 100B is in a range of 5 μm to 1 mm. Such embodiments may be useful for, for example, in detecting analytes such as cells and bacteria.

The insulating substrate 100, nanopore 110 and nanopore electrode 120 described above may be fabricated by a number of different methods. In some embodiments, the insulating substrate 100, nanopore 110 and nanopore electrode 120 may be fabricated as follows. First, a clean glass ($SiO_2$) substrate is coated with a thin metal layer. The thin metal layer may be deposited on the glass substrate using a thin film deposition technique such as atomic layer deposition (ALD), sputtering, evaporation, and the like. The metal layer then undergoes a lithographic process (e.g., E-Beam lithography or photolithography) resulting in the formation of a circular dot (e.g., of ~50 nm to 5 μm in diameter) along with an electrical lead extending therefrom. Subsequently, a layer of $SiO_2$ (e.g., 2 μm) may be coated atop the metal dot and the base $SiO_2$ layer as the cover layer (e.g., using an ALD method). With such a prepared substrate, a nanopore-forming process may be used to make the nanopore that traverses the $SiO_2$ layer, thin metal layer and glass substrates, whereby the metal portion of the nanopore forms the embedded metal ring within the insulating substrate that may act as an EDL capacitor. One method for forming such a nanopore is electron beam stimulated decomposition and sputtering, such as with a JEOL 2010F transmission electron microscope. Formation of a nanopore using this process is shown in Ho et al., *PNAS*, 102, 30, 10445-10450 (2005), the disclosure of which is incorporated herein in its entirety by reference.

Referring again to FIG. 1, provided according to embodiments of the invention are methods of determining a nucleotide sequence of a polynucleotide 180. In some embodiments, the methods include measuring capacitances between a nanopore electrode 120 and reference electrode 140 in contact with an electrolyte 130 as the polynucleotide 180 translocates a portion of the electrolyte 130 at a surface of the nanopore electrode 120; and correlating the measured capacitances with nucleotides of the polynucleotide 180. In some embodiments, each nucleotide of the polynucleotide 180 may translocate the portion of the electrolyte 130 at the surface of the nanopore electrode 120 at a particular time, such that the EDL capacitances associated with each particular nucleotide and the electrolyte 130 surrounding it may be measured. In some embodiments wherein the polynucleotide is double stranded DNA, a base pair (e.g, G-C or A-T) may translocate the portion of the electrolyte 130 at the surface of the nanopore electrode 120 at a particular time, such that the EDL capacitances associated with each particular base pair and the electrolyte 130 surrounding it may be measured.

In particular embodiments, methods of determining a nucleotide sequence of a polynucleotide 180 include (i) inducing the polynucleotide 180 to translocate through a nanopore 110 of an EDL capacitive device according to an embodiment of the invention; (ii) measuring capacitances between the nanopore electrode 120 and the reference electrode 140 of the EDL capacitive device as the polynucleotide 180 translocates through the nanopore 110; and (iii) correlating the measured capacitances as the polynucleotide 180 translocates through the nanopore 110 with nucleotides of the polynucleotide 180.

A polynucleotide 180 may include single or multiple stranded configurations, where one or more of the strands may or may not be completely aligned with another. In particular embodiments, the polynucleotide 180 is single stranded. Examples of polynucleotides include DNA (including cDNA), RNA, oligonucleotides, and PNA and other polynucleotides. The polynucleotides may also include analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and polynucleotides (or synthetic or naturally occurring analogs) in which one or more of the conventional bases has been replaced with a group (natural or synthetic) capable of participating in hydrogen bonding interactions, such as Watson-Crick type, Wobble type and the like. A "nucleotide" refers to a sub-unit of a polynucleotide, which has a phosphate group, a five carbon sugar and a nitrogen-containing base (a nucleobase), and also refers to functional analogs (whether synthetic or naturally occurring) of such sub-units.

Inducing the polynucleotide 180 to translocate through the nanopore 110 may be achieved by any suitable method. However, in some embodiments, a bias potential, may be generated by driver circuit 170 such that a polynucleotide 180 in the electrolyte 130 may be induced to translocate the nanopore 110. For example, DNA and RNA are negatively charged and so may be induced to translocate the nanopore 110 based on electrostatic attraction or repulsion.

The electrical double layer (EDL) of the nanopore electrode 120B includes a compact layer, which is a surface-localized portion, and a diffuse layer, which is a mobile and spatially distributed portion. Under normal circumstances, the compact layer is made up of localized charges, including electrons, solvent molecules, and/or specifically adsorbed ions, and the diffuse layer is made up of various solvated electroactive and inactive ions. These charged species may cause the EDL structure to behave like a capacitor. During translocation of polynucleotide, the backbone moiety and the individual nucleotides along with the companion ionic species in the surrounding electrolyte may occupy the EDL.

Because of this electrochemical nature, an EDL-capacitive device may be particularly sensitive to changes in the charge and dielectric conditions of the electrolyte 130. When a nucleobase translocates directly through a nanopore electrode 120, as described above, the nature of the charged species, along with the corresponding change in the dielectric of the surrounding electrolyte 130, of the nucleobase should produce a capacitance reading specific to its base type. Referring to FIG. 2, the narrow thickness 200 of the conductive ring in the EDL capacitive device may give rise to matching dimensions between the sensor and the inter-base-distance of DNA, estimated to be around 0.5-0.6 nm during DNA translation. The EDL capacitive device may be particularly sensitive to the charge and dielectric state of the electrolyte 130 surrounding the base structure translocated in the center of nanopore electrode 120 due to the elevated electrical field in the center. Because of this, the bases located either above or below the nanopore electrode 120 will have reduced contributions to the measured signals. This unique feature may be used to resolve information about the neighboring base structures through signal deconvolution in post data analysis. The resolved information may be used to minimize potential reading errors. Furthermore, the axisymmetric nature of a nanopore electrode 120 that is shaped as a conductive ring 120B makes it possible to have a uniform contribution (to the measured signals) from the backbone of DNA. This feature allows for filtering out the baseline signal from the backbone, thus leading to a highly sensitive way to discriminate between the nucleobases.

Another advantage of an EDL capacitive device according to embodiments of the invention is that the nanopore electrode 120 electrode may also be used as an electrode for redox purposes. This unique feature may become desirable because the two purine bases are prone to electrochemical oxidation. When oxidation (i.e., electron transfer) of the base occurs, a lower capacitance value is expected. This information can be used to separate the purines (A & G) from the pyrimidines (T & C).

The devices and methods described herein may also be used with other polymers, whether organic or inorganic, to determine the monomer sequence of the polymer. In some embodiments, the polymer is a linear polymer. For example, a polypeptide or oligopeptide, including both natural and/or synthetic amino acids, may be sequenced after denaturizing to form a linear polymer chain.

As such, in some embodiments of the invention, provided are electrical double layer (EDL) capacitive devices that include an insulating substrate defining a nanopore therethrough; a nanopore electrode exposed in a portion of the nanopore; an electrolyte in contact with the nanopore electrode; a reference electrode in electrical contact with the electrolyte; and a meter electrically coupled between the nanopore electrode and the reference electrode, wherein the meter is configured to measure capacitances between the nanopore electrode and the reference electrode, and wherein the meter is further configured to correlate different measured capacitances with different monomers of a polymer.

Also provided are methods of determining a monomer sequence of a polymer, that include (i) inducing the polymer to translocate through a nanopore of an EDL capacitive device that includes (a) an insulating substrate defining the nanopore therethrough; (b) a nanopore electrode exposed in a portion of the nanopore; (c) an electrolyte in contact with the nanopore electrode; and (d) a reference electrode in electrical contact with the nanopore electrode; (ii) measuring capacitances between the nanopore electrode and the reference electrode as the polymer translocates through the nanopore; and (iii) correlating the measured capacitances as the polymer translocates through the nanopore with monomers of the polymer. Furthermore, also provided are methods of determining a monomer sequence of a polymer that include measuring capacitances between a nanopore electrode and an electrolyte in contact with the nanopore electrode as the polymer translocates a portion of the electrolyte at a surface of the nanopore electrode; and correlating the measured capacitances with monomers of the polymer.

In some embodiments, the devices and methods described herein may also be used to detect analytes or properties thereof. For example, in some embodiments of the invention, provided are electrical double layer (EDL) capacitive devices that include an insulating substrate defining a nanopore therethrough; a nanopore electrode exposed in a portion of the nanopore; an electrolyte in contact with the nanopore electrode; a reference electrode in electrical contact with the electrolyte; and a meter electrically coupled between the nanopore electrode and the reference electrode, wherein the meter is configured to measure capacitances between the nanopore electrode and the reference electrode, and wherein the meter is further configured to correlate different measured capacitances with the identity and/or property of an analyte.

Also provided herein are methods of determining the presence and/or property of an analyte that include (i) inducing the analyte to translocate through a nanopore of an EDL capacitive device that comprises (a) an insulating substrate defining the nanopore therethrough; (b) a nanopore electrode exposed in a portion of the nanopore; (c) an electrolyte in contact with the nanopore electrode; and (d) a reference electrode in electrical contact with the nanopore electrode; (ii) measuring capacitances between the nanopore electrode and the reference electrode as the analyte translocates through the nanopore; and (iii) correlating the measured capacitances as the analyte translocates through the nanopore with identity and/or property of the analyte.

Further provided according to some embodiments of the invention are methods of determining the presence and/or a property of an analyte that include measuring capacitances between a nanopore electrode and an electrolyte in contact with the nanopore electrode as the analyte translocates a portion of the electrolyte at a surface of the nanopore electrode; and correlating the measured capacitances with the identity and/or property of the analyte.

As used herein, the term "analyte" refers to a chemical or biological entity that can be identified, detected and/or quantified by EDL capacitance. As such, the polynucleotides and polymers described herein are also analytes. In these cases, theses molecules are typically detected by the change in EDL capacitance as the monomers and/or nucleotides that form the molecules translocate a portion of the electrolyte at the surface of a nanopore electrode. However, in other cases, the analyte may be detected, either in part or in whole, via the change in EDL capacitance as aggregate portions of the analyte translocate a portion of the electrolyte at the surface of a nanopore electrode. By the term "aggregate portions," it is meant that a plurality of subunits or monomers of the analyte may translocate a portion of the electrolyte at the surface of a nanopore electrode at one time. As such, in some cases, the analyte may not be detected by sequencing of the constituent monomers but by a signature change in the EDL capacitance that may be correlated with the translocation of a particular analyte, or an analyte with a particular property, through electrolyte at the surface of the nanoelectrode.

The analyte may be biological or non-biological, unless otherwise specified. A "biological analyte" includes microorganism, cells, cell products, or biological molecules, or any other biological analyte known to those of ordinary skill in the art.

A "microorganism" refers to a microscopic living system. Examples of microorganisms include viral particles such as virions, prions or viriods; bacteria; fungi; archea; protists; microscopic algae; plankton; and planarian. A "cell" includes both prokaryotic and eukaryotic cells, including both natural and recombinant cells. Cell products include constituents of cells such as cell membranes and organelles. A "biological molecule" refers to a molecule that is produced by a living organism, and also refers to synthetic analogs of such molecules. Examples of biological molecules include carbohydrates such as glucose, disaccharides and polysaccharides; proteins; lipids (including lipid bilayers); and nucleic acids (polynucleotides), such as DNA and RNA. Biological molecules may also be small molecules, including monomers and oligomers of other biological molecules, e.g., nucleic acids, nucleotides, fatty acids, etc. The biological molecules may be naturally occurring or synthetic, or may include both naturally occurring and synthetic portions. Thus, the term biological molecule also includes derivatives such as conjugated nanoparticles of biological molecules. Other biological polymer may also be sequenced by methods described herein.

A "non-biological analyte" refers to molecules and entities that are not a biological molecules, as defined above. Such molecules may be organic in some embodiments, or inorganic in some embodiments, or a combination of organic and inorganic moieties. A non-biological molecule may be synthetic or naturally occurring. As an example, some synthetic polymer nanoparticles may be non-biological in nature. Some other polymers that may be sequenced by the methods described herein may also be non-biological in nature.

Recently, a computational approach to simulate the electrochemical processes of nanometer electrodes based on a finite element analysis was developed by the inventor of the present application. See Yang X. and Zhang G., *Nanotechnology*, 18, 335201, 1-9, (2007), which is incorporated by reference in its entirety. A brief description of this computational approach and the results of this study follow. For the electrochemical environment surrounding a nanometer spherical electrode 300 shown in FIG. 3A, a cyclic electrical overpotential (E) is applied to the nanometer electrode 300 (radius=1 nm) to polarize the electrode 300 and the surrounding EDL structure as well as the electrolyte 310. The resulting electrical field ($\phi$) surrounding the electrode is determined. The EDL capacitance is calculated using the following formula:

$$C_{EDL} = \varepsilon\varepsilon_0 \left( \frac{\partial^2 \phi}{\partial r \cdot \partial E} \right).$$

See, Bard and Faulkner, *Electrochemical Methods*, John Wiley & Sons, Inc. 2001.

As schematically shown in FIG. 3B, a two-dimensional (2D) quarter-circle geometric model in a cylindrical coordinate system (u, v) is considered to represent a three-dimensional (3D) spherical electrode 300 by taking advantage of the axisymmetery (about the u-axis) and the in-plane symmetry (about the v-axis). In this model, an electrode 300 of radius $r_0$ is placed at the origin of the coordinate system. The space surrounding the electrode 300 is divided into two domains: the first represents the electronic compact layer of the EDL of the electrolyte 310 located within $r_0 \leq r < r_0 + \mu$ (note $r = \sqrt{(u^2 + v^2)}$), and the second represents the electrolyte 310 located between $r = r_0 + \mu$ and $r = 1000 r_0$. Inside the compact layer, there is an inner Helmholtz plane (IHP) and an outer Helmholtz plane (OHP). In the calculations, it is assumed that there is no specific ionic adsorption at the surface of the electrode 300; thus, the region inside the IHP is mainly filled with solvent molecules without any ions. Furthermore, it is also assumed that the OHP is the plane of closest approach for all the ions (active and inactive), and is the position of electron transfer, which means that electron transfer between the electrode 300 and the electrolyte 310 occurs here. Referring to FIG. 3C, it is assumed that the dielectric constant ∈ varies smoothly and continuously inside the compact layer of the electrolyte 310.

Figure 4A:
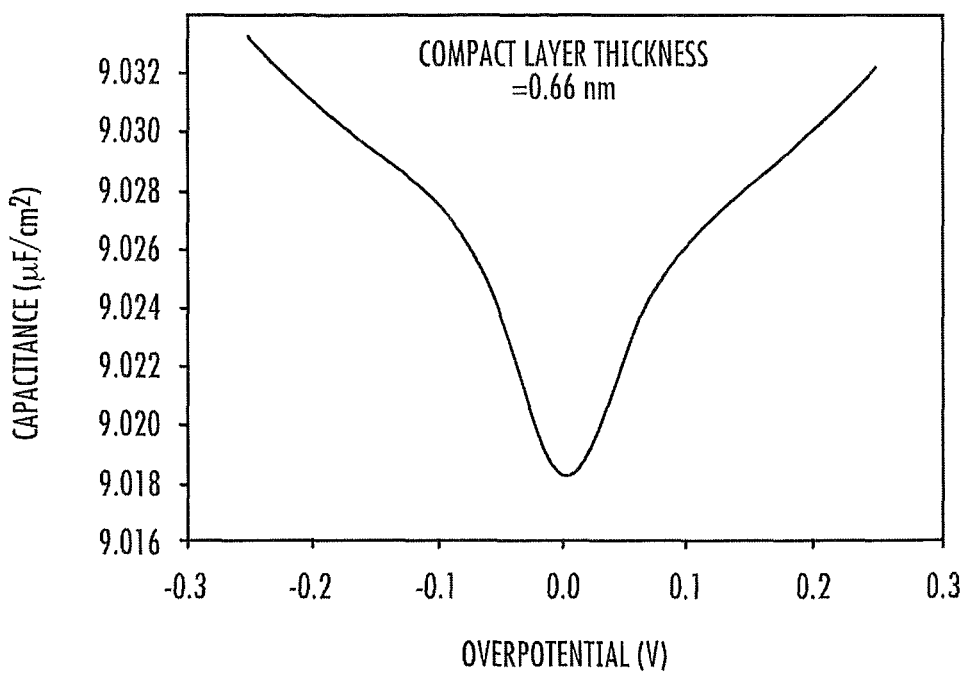
FIG. 4A and FIG. 4B provide typical curves for the variation of EDL capacitance with electrical overpotential for two cases.
Figure 4B:
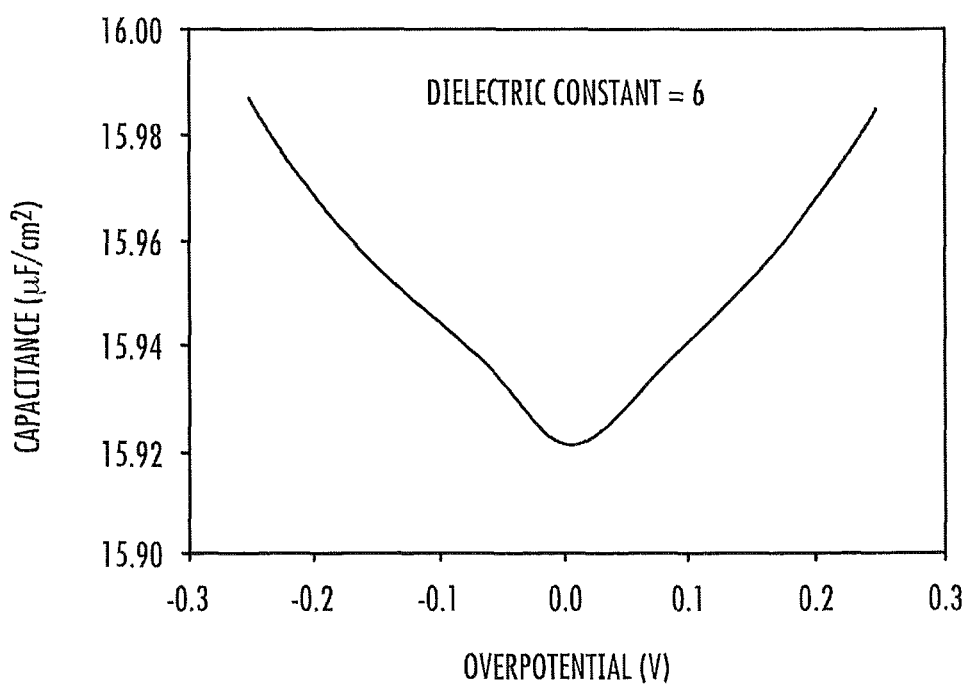
Figure 5:
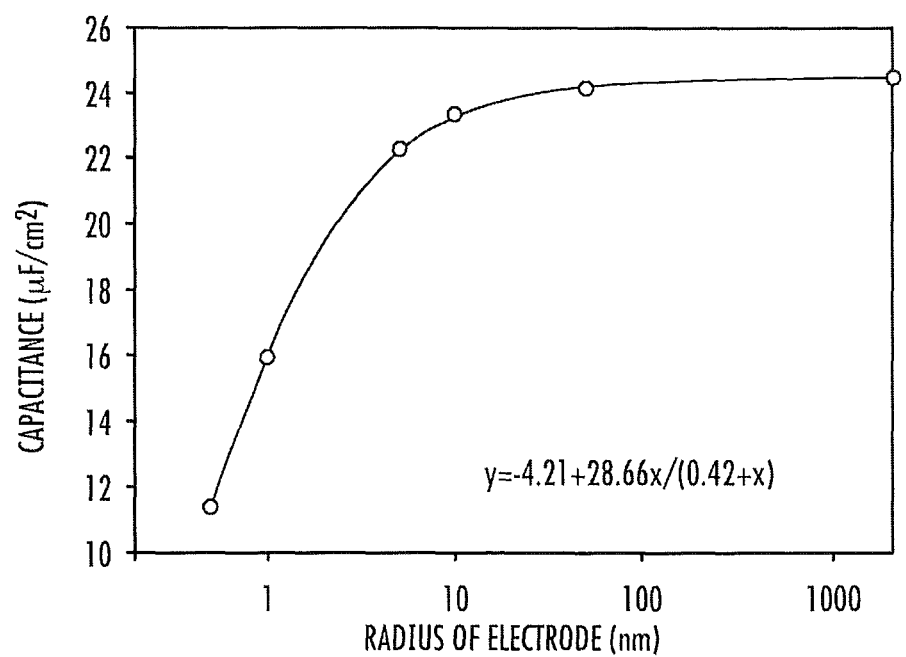
FIG. 5 is a graph depicting the variation of EDL capacitance with the radius of the electrode.
Figure 6:
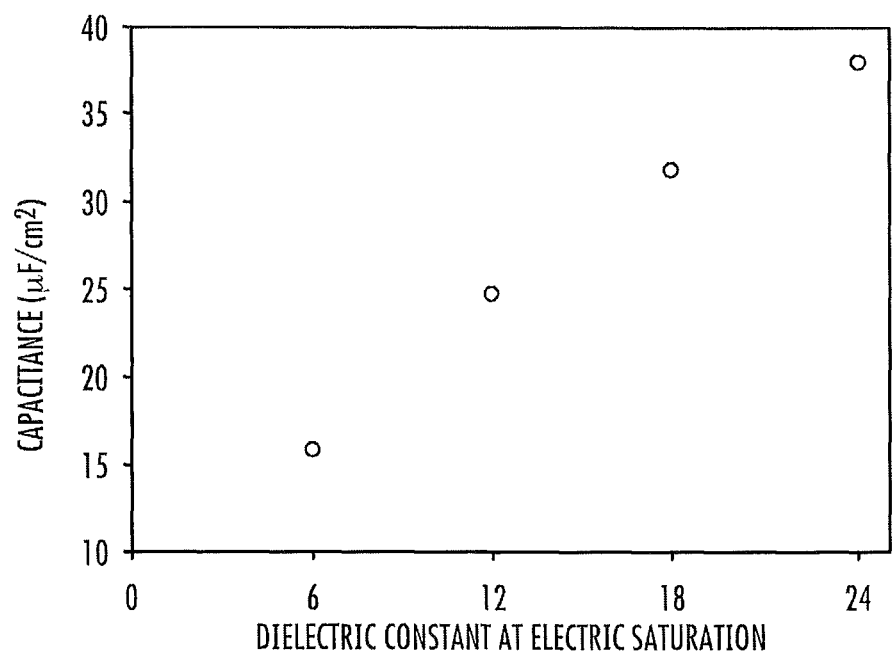
FIG. 6 is a graph depicting the variation of EDL capacitance with the dielectric constant at electrical saturation.
Figure 7:
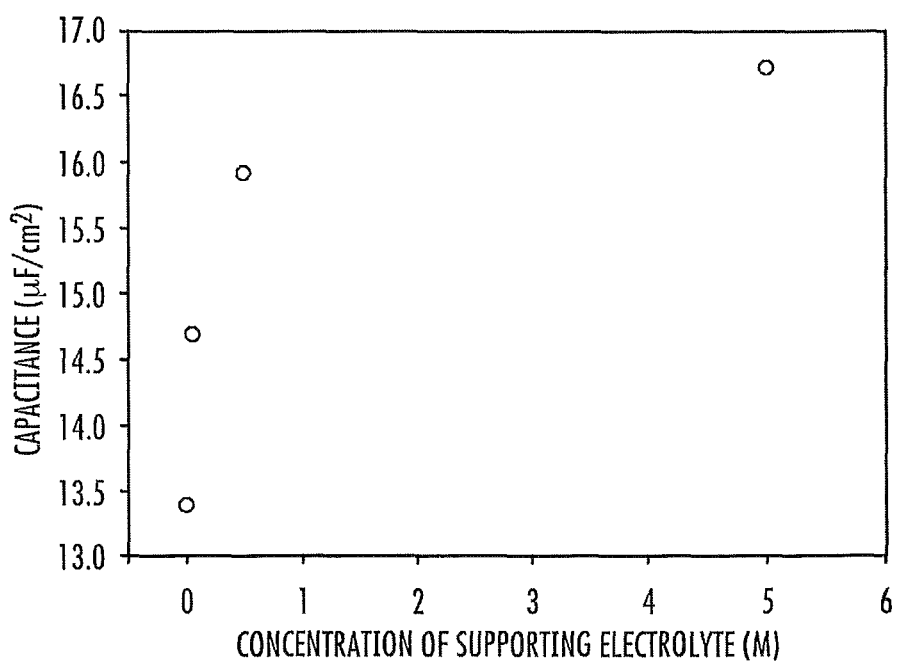
FIG. 7 is a graph depicting the variation of EDL capacitance with the concentration of the supporting eletrolyte.
Figure 8:
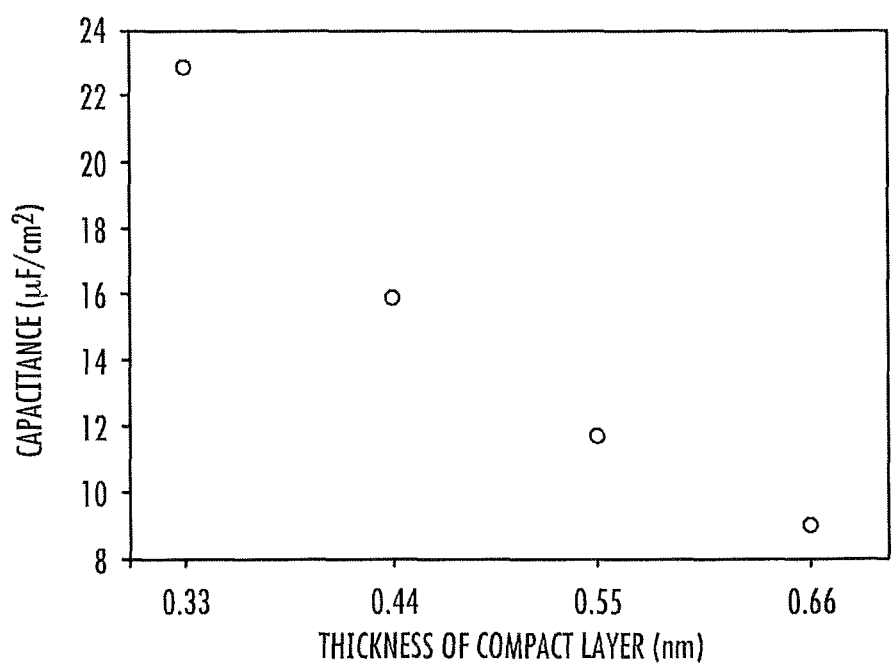
FIG. 8 is a graph depicting the variation of EDL capacitance with the thickness of the compact layer.

Selected results obtained from these computational analyses are provided in FIG. 4 through FIG. 8. FIG. 4 shows two examples in which the EDL capacitance as a function of overpotential is plotted when the compact layer thickness (CLT) is 0.66 nm and the dielectric constant (∈) is 6 (FIG. 4A) and when the CLT is 0.44 nm and ∈ is 6 (FIG. 4B). FIG. 5 is a graph depicting the variation of EDL capacitance with the radius of the electrode. FIG. 6 is a graph depicting the variation of EDL capacitance with the dielectric constant at electrical saturation. FIG. 7 is a graph depicting the variation of EDL capacitance with the concentration of the supporting eletrolyte. FIG. 8 is a graph depicting the variation of EDL capacitance with the thickness of the compact layer.

This data shows that the capacitance of the EDL structure surrounding a nanometer electrode 300 is heavily influenced by changes in dielectric constant in the compact layer and diffuse layer, as well as compact layer thickness and the bulk electrolyte concentration. Thus, since the compact layer and the nearby diffuse layer have dimensions on the scale of several angstroms to a few nanometers, a nanoelectrode 300 can be used to discriminate changes in the charge and dielectric state in an electrolyte 310 spanning from the nanopore electrode 300 surface to a few nanometers out.

As shown in FIG. 8, an increase in the thickness ($\mu$) of the compact layer surrounding a 1-nm spherical electrode from 0.33 to 0.66 nm has caused a drastic drop in capacitance from about 23 to 9 $\mu F/cm^2$. Further, an increase in dielectric constant (8) at the electrode surface from 6 to 24 has caused a significant increase in capacitance from about 16 to 38 $\mu F/cm^2$ (See FIG. 6). As a reference, $\mu$ usually varies from 0.3 to 0.7 nm depending on the size of the ionic species in the electrolyte; ∈ changes from 6 for a highly saturated ionic electrolyte to 78 for water. Thus, the charge (both electronic and ionic) distribution and the dielectric profile in the compact layer and in the nearby diffuse layer affect the electrical property of the EDL structure in a very sensitive way.

Thus, an EDL capacitive device of the invention may be able to detect single nucleobases of a polynucleotide as they pass through the EDL of a nanopore electrode according to an embodiment of the invention by detecting the change in capacitance. Further, the sensitivity of the EDL should allow for identity of the nucleobase to be determined based on the measured capacitance as the nucleobase translocates through the EDL at the surface of the nanopore electrode. Therefore, in some embodiments of the invention, an EDL capacitive device that has the advantages of nanopore sequencing, namely low cost and high throughput sequencing, and is sensitive enough to detect single bases of a polynucleotide, may be provided. Such sensitivity may then also be useful for detection of monomers that form other polymers, and for the detection of other types of analytes.

In the drawings and specification, there have been disclosed typical embodiments of the invention and, although specific terms are employed, they are used in a generic and descriptive sense only and not for purposes of limitation, the scope of the invention being set forth in the following claims.

EXAMPLES

Example 1

To demonstrate that a simple EDL device can be used as a sensor to detect surface ionic and molecular events, a circular flat-gold-disc electrode (d=1.6 mm) in 0.5 M $H_2SO_4$ solution was used to examine adsorption of sulfate and bisulfate ions on the electrode surface. A $H_2SO_4$ solution was chosen because of the extensive literature on the adsorption of sulfate and bisulfate using various spectroscopic techniques and scanning tunnelling microscopy (STM).

Figure 9:
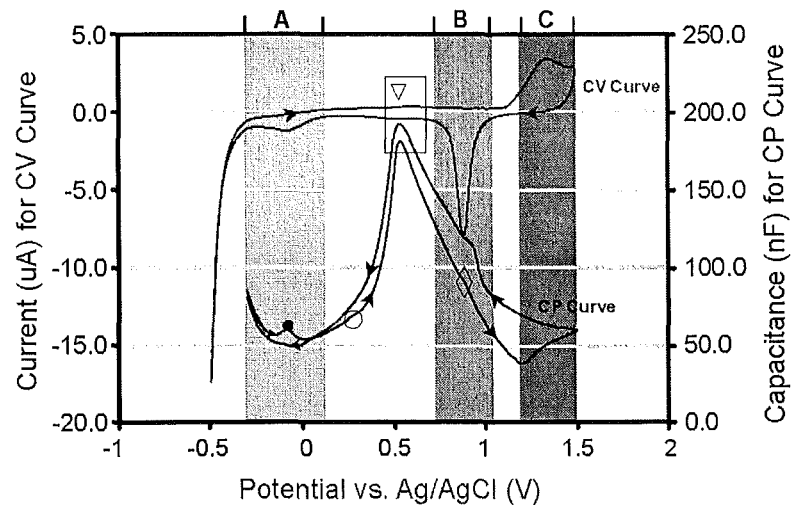
FIG. 9 is a graph depicting the capacitance potential (CP) and cyclic-voltammetry (CV) curves for a polycrystalline gold surface in 0.5M $H_2SO_4$.

In the obtained capacitance-potential (CP) curve (See FIG. 9), starting at approximately −0.3 V in the forward scan direction, the first characteristic feature at approximately −0.14 V (marked by ●) is denoted as reorientation of water molecules at the Au surface in an acidic solution. As Parry (Parry D., Samant M. G., Seki S. H., Philpott M. R., Ashley K. 1993. *Langmuir*, 9, 1878) first reported in Plasmon resonance studies, the hydrogen end of a water molecule attaches to the surface at −0.2 V and the oxygen end attaches to the surface at a higher potential. The small notch at approximately 0.24 V (marked by O) is attributed to the potential of zero charge (PZC) of the Au surface, which is accepted to be approximately 0.17-0.3 V under similar conditions. From that point, capacitance increases as potential increases due to increased accumulation of charged ions in the double layer. At approximately 0.54 V (marked by □ with ∇), capacitance begins to decrease in a sharp, downward V-turn manner, marking the onset of adsorption of sulfate and bisulfate ions to the Au surface, which causes a reduction in the dielectric constant at the electrode surface and thus lowers the capacitance. At the same potential in the corresponding cyclic voltammetric (CV) curve, a slight current peak is visible, confirming the electron transfer event for facilitating the adsorption of these ions. The mass-change result by Jusys (Jusys Z. and Bruckenstein S. 1998. *Electrochemical Solid-State Letters*, 1, 74) supports this argument in which the increase in surface mass starts to take off at a similar potential. That the surface adsorption feature is so prominently reflected in the CP curve and not in the CV curve suggests the uniquely sensitive nature of the EDL capacitive effect to surface interaction events. The notch at approximately 0.85 V (marked by ◊), is attributed to the hydronium ($H_3O^+$) assisted lattice formation of sulfate ions. This is consistent with the STM results obtained by Kolb (Kolb D. M. 2001. *Angew Chem*, 40, 1162) in which the sulfate and hydronium ions co-formed a lattice structure in conforming with the underlying Au(111) crystalline structure when the potential transition from 0.65 V to 0.8 V. At approximately 1.2 V, an upward V-turn feature in the CP curve marks the oxidation of the gold surface. When the potential is scanned backward, the transitional feature of Au-oxide reduction is clearly evident. Moving further left, the cleavage of the adsorbed sulfate and bisulfate ions begins until their total desorption at the downward V-turn point. After that, the CP curve drops drastically until hydrogen adsorption begins, which appears to prevent water reorientation from occurring because of the absence of the distinct water-reorientation feature.

Example 2

Figure 10:
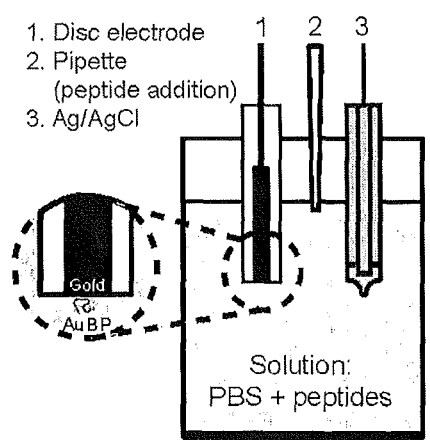
FIG. 10 illustrates a set up for peptide binding studies.
Figure 11A:
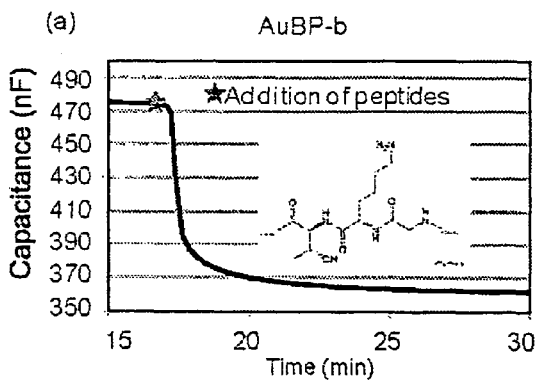
FIG. 11a is a graph depicting the time-dependent EDL capacitance measurement during the binding of AuBP-b to Au surface.

To show that an EDL sensor can be used to characterize biomolecules such as proteins or peptides, we conducted peptide binding studies. Using a test setup (See FIG. 10), capacitance of the Au disc electrode was measured while an aliquot (60 µl) of solution containing gold binding peptides (AuBP; at 1 mg/ml) was added through a pipette to the PBS solution (20 ml 0.1 M PBS). Two types of measurements were taken: 1) time-dependent capacitance when the electrode was held at 0 V, and 2) potential-dependent capacitance. For this study, two types of Au binding peptides were examined: a short peptide with 12 amino acids (AuBP-a: WAGAKRLVL-RRE) and a long peptide made of three repeats of the short one (AuBP-b). FIG. 11A shows the binding characteristics over time for AuBP-b peptides at the Au surface. Because peptides were injected to the solution surface, their diffusion down to the vicinity of the electrode surface took some time. Upon their arrival, the EDL sensor responded immediately with a very significant decrease in the capacitance value. This decrease in capacitance value is the result of the fast binding of the peptides to the Au surface, thus lowering the dielectric constant of the electrolytic domain at the electrode surface. The kinetic characteristics of the peptide binding suggest that even at a low peptide concentration (0.7 µM), the capacitance measurements can rapidly and sensitively capture the biding of peptides to the Au surface in real time.

Figure 11B:
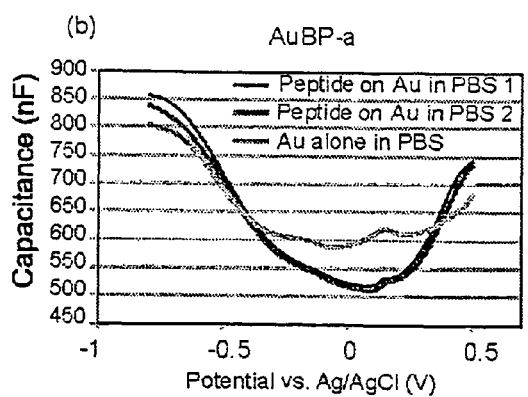
FIG. 11b is a graph depicting the capacitance potential curve for AuBP-a bound surfaces.
Figure 11C:
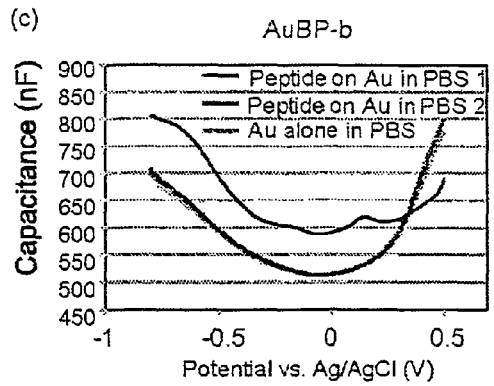
FIG. 11e is a graph depicting the capacitance-potential curve for AuBP-b bound Au surfaces.

After the capacitance reading stabilized over time, we varied the electrode potential from −0.8 V to +0.5 V while measuring the corresponding capacitance. FIG. 11B and FIG. 11C show the CP measurements for AuBP-a and AuBP-b peptides respectively and a control (without peptides). Though the two replicate curves in each graph show good repeatability of capacitance measurements, two sets of curves differ from each other in shape and characteristic CP fingerprints. With respect to control, the binding of AuBP-a (FIG. 11C) caused capacitance to drop only between −0.4 V to 0.3 V, while the binding of AuBP-b (FIG. 11C) caused capacitance to drop across the entire range of potential values less than 0.3 V. Moreover, the characteristic feature of the PZC of a bare gold surface seen at approximately 0.2 V is still visible with the AuBP-a, but not with the AuBP-b, indicating that the binding of AuBP-b peptides altered the gold surface. In fact, the binding of AuBP-b shifts the PZC of the peptide-bound gold surface to approximately-0.05 V (cf. around 0.2 V for bare gold). This may be expected when considering the chain-length difference in the two types of peptides: Because AuBP-a peptides are short-chain amino acids, and AuBP-b peptides are three times longer, the PZC of the bare Au surface is still visible in the AuBP-a bound gold surface, but not in the AuBP-b bound gold surface.

The shape of the CP curves provides information on the peptide composition and conformation. For example, in the AuPB-b case (FIG. 11C), the bound surface carried positive charges when the electrode potential was above the PZC (−0.05 V) and negative charges when the potential was below the PZC. Thus at the PZC, the peptides are thought to bind to the gold surface laterally, with positive and negative polar groups (H, O, and OH; FIG. 11A inset) both acting, with equal likelihood, as binding sites. At a potential below the PZC the positive groups of the peptide are likely to provide the binding anchorage. At a potential above the PZC the negative groups of the peptide are to provide the binding anchorage. Thus, the CP curve's asymmetry with respect to the PZC suggests the asymmetric chemical composition in terms of the positive and negative groups in the peptides. These results allows us to infer that the positive groups in the amino acid chains hold the peptides closer to the gold surface than the negative groups, thus producing a slightly lower capacitance reading at a potential below the PZC, compared with that of an opposite potential above the PZC. At approximately 0.32 V, the CP curves for gold surfaces, both with and without peptide binding, intersect: We thus infer that beyond that point, adsorption of negative ions (mostly Cl⁻) at the gold surface was hindered at the peptide-bound surface, which could otherwise have brought the capacitance reading a bit lower, as was the case without the peptides.

The invention claimed is:

1. An electrical double layer (EDL) capacitive device comprising:
    an insulating substrate defining a nanopore therethrough;
    a nanopore electrode exposed in a portion of the nanopore, wherein the nanopore electrode defines a conductive ring surface exposed around an inner surface of the nanopore along its depth in a conductive ring;
    an electrolyte in contact with the nanopore electrode;
    a reference electrode in electrical contact with the electrolyte; and
    a meter electrically coupled between the nanopore electrode and the reference electrode,
    wherein the meter is configured to measure the EDL capacitance between the nanopore electrode and the reference electrode at a first time and to correlate the first measured EDL capacitance with
        (a) one or more properties of an analyte;
        (b) the identity of the analyte; or
        (c) one or more properties of the analyte and the identity of the analyte.

2. The EDL capacitive device of claim 1, wherein the conductive ring has a thickness in a range of about 1 Å to about 1 nm.

3. The EDL capacitive device of claim 1, wherein the conductive ring has a diameter in a range of about 0.5 nm to about 2.5 nm.

4. The EDL capacitive device of claim 1, further comprising a driver circuit configured to generate a biasing potential across the nanopore to induce the analyte to translocate through the nanopore.

5. The EDL capacitive device of claim 1, wherein the analyte is a polynucleotide and the meter is configured to correlate the first measured EDL capacitance with the presence of a first nucleotide in said polynucleotide.

6. The EDL capacitive device of claim 5, wherein the meter is further configured to measure the EDL capacitance between the nanopore electrode and the reference electrode at a second time and to correlate the second measured EDL capacitance with the presence of a second nucleotide in said polynucleotide.

7. The electrical double layer (EDL) capacitive device of claim 1, wherein the insulating substrate comprises a first insulating layer, and wherein the nanopore electrode comprises a conductive layer on the first insulating layer, and the EDL capacitive device further comprises:
    a second insulating layer on the conductive layer so that the conductive layer is between the first and second insulating layers, and wherein the nanopore extends through the first and second insulating layers and through the conductive layer so that portions of the conductive layer are exposed in the nanopore between the first and second insulating layers.

8. The EDL capacitive device of claim 7, wherein each of the first and second insulating layers comprises at least one insulating material selected from the group consisting of silicon dioxide, silicon nitride and polyxylylene polymers.

9. The EDL capacitive device of claim 7, wherein the conductive layer comprises at least one material selected from the group consisting of platinum, gold, titanium, copper, carbon, indium tin oxide and a conductive polymer.

10. The EDL capacitive device of claim 7, wherein the electrolyte comprises at least one of KCl, NaCl and PBS.

11. The EDL capacitive device of claim 7, wherein a width of a portion of the nanopore through the first insulating layer is greater than a width of a portion of the nanopore through the nanopore electrode, and wherein a width of a portion of the nanopore through the second insulating layer is greater than a width of the portion of the nanopore through the nanopore electrode.

12. The EDL capacitive device of claim 1, wherein the conductive ring surface exposed around the inner surface of the nanopore along its depth in a conductive ring is located at the center of the nanopore.

13. A plurality of EDL capacitive devices of claim 1.

14. A method of determining a nucleotide sequence of a polynucleotide, comprising:
(i) inducing the polynucleotide to translocate through a nanopore of an EDL capacitive device that comprises
(a) an insulating substrate defining the nanopore therethrough;
(b) a nanopore electrode exposed in a portion of the nanopore, wherein the nanopore electrode defines a conductive ring surface exposed around an inner surface of the nanopore along its depth in a conductive ring;
(c) an electrolyte in contact with the nanopore electrode;
(d) a reference electrode in electrical contact with the electrolyte; and
(e) a meter electrically coupled between the nanopore electrode and the reference electrode;
(ii) measuring EDL capacitances between the nanopore electrode and the reference electrode as the polynucleotide translocates through the nanopore; and
(iii) correlating the measured EDL capacitances as the polynucleotide translocates through the nanopore with nucleotides of the polynucleotide.

15. The method of claim 14, wherein the insulating substrate comprises a first insulating layer, and wherein the nanopore electrode comprises a conductive layer on the first insulating layer, the EDL capacitive device further comprises:
a second insulating layer on the conductive layer so that the conductive layer is between the first and second insulating layers, and wherein the nanopore extends through the first and second insulating layers and through the conductive layer so that portions of the conductive layer are exposed in the nanopore between the first and second insulating layers.

16. A method of determining a nucleotide sequence of a polynucleotide comprising:
measuring EDL capacitances between (a) a nanopore electrode defining a conductive ring surface exposed around an inner surface of the nanopore along its depth in a conductive ring, and (b) an electrolyte in contact with the nanopore electrode as the polynucleotide translocates a portion of the electrolyte at a surface of the nanopore electrode; and
correlating the measured EDL capacitances with nucleotides of the polynucleotide.

17. The method of claim 16, wherein one nucleotide of the polynucleotide translocates the portion of the electrolyte at the surface of the nanopore electrode at a time when a nucleotide is positioned inside the nanopore electrode.

18. A method of determining a monomer sequence of a polymer, comprising:
(i) inducing the polymer to translocate through a nanopore of an EDL capacitive device that comprises
(a) an insulating substrate defining the nanopore therethrough;
(b) a nanopore electrode exposed in a portion of the nanopore, wherein the nanopore electrode defines a conductive ring surface exposed around an inner surface of the nanopore along its depth in a conductive ring;
(c) an electrolyte in contact with the nanopore electrode;
(d) a reference electrode in electrical contact with the nanopore electrode; and
(e) a meter electrically coupled between the nanopore electrode and the reference electrode;
(ii) measuring EDL capacitances between the nanopore electrode and the reference electrode as the polymer translocates through the nanopore; and
(iii) correlating the measured EDL capacitances as the polymer translocates through the nanopore with monomers of the polymer.

19. A method of determining a monomer sequence of a polymer comprising:
measuring EDL capacitances between (a) a nanopore electrode defining a conductive ring surface exposed around an inner surface of the nanopore along its depth in a conductive ring, and (b) an electrolyte in contact with the nanopore electrode as the polymer translocates a portion of the electrolyte at a surface of the nanopore electrode; and
correlating the measured EDL capacitances with monomers of the polymer.

20. An electrical double layer (EDL) capacitive device comprising:
an insulating substrate defining a nanopore therethrough;
a nanopore electrode exposed in a portion of the nanopore, wherein the nanopore electrode defines a conductive ring surface exposed around an inner surface of the nanopore along its depth in a conductive ring;
an electrolyte in contact with the nanopore electrode;
a reference electrode in electrical contact with the electrolyte; and
a meter electrically coupled between the nanopore electrode and the reference electrode,
wherein the meter is configured to measure EDL capacitances between the nanopore electrode and the reference electrode, and
wherein the meter is further configured to correlate different measured EDL capacitances with different monomers of a polymer.

21. A method of determining the presence of, the identity of and/or a property of an analyte, comprising:
(i) inducing the analyte to translocate through a nanopore of an EDL capacitive device that comprises
(a) an insulating substrate defining the nanopore therethrough;
(b) a nanopore electrode exposed in a portion of the nanopore, wherein the nanopore electrode defines a conductive ring surface exposed around an inner surface of the nanopore along its depth in a conductive ring;

(c) an electrolyte in contact with the nanopore electrode; and (d) a reference electrode in electrical contact with the electrolyte;

(ii) measuring EDL capacitances between the nanopore electrode and the reference electrode as the analyte translocates through the nanopore; and (iii) correlating the measured EDL capacitances as the analyte translocates through the nanopore with
  (a) one or more properties of the analyte;
  (b) the identity of the analyte; or
  (c) one or more properties of the analyte and the identity of the analyte.

22. The method of claim 21, wherein the analyte comprises a virus, cell and/or a bacteria.

23. A method of determining the presence of, the identity of and/or a property of an analyte comprising:

measuring EDL capacitances between a nanopore electrode defining a conductive ring surface exposed around an inner surface of the nanopore along its depth in a conductive ring, and (b) an electrolyte in contact with the nanopore electrode as the analyte translocates a portion of the electrolyte at a surface of the nanopore electrode; and correlating the measured EDL capacitances with
  (a) one or more properties of the analyte;
  (b) the identity of the analyte; or
  (c) one or more properties of the analyte and the identity of the analyte.

24. The method of claim 23, wherein the analyte comprises a virus, cell and/or a bacteria.

25. An electrical double layer (EDL) capacitive device comprising:

an insulating substrate defining a nanopore therethrough;

a nanopore electrode exposed in a portion of the nanopore, wherein the nanopore electrode defines a conductive ring surface exposed around an inner surface of the nanopore along its depth in a conductive ring;

an electrolyte in contact with the nanopore electrode;

a reference electrode in electrical contact with the electrolyte; and a meter electrically coupled between the nanopore electrode and the reference electrode, wherein the meter is configured to measure EDL capacitances between the nanopore electrode and the reference electrode, and wherein the meter is further configured to correlate different measured EDL capacitances with the identity of an analyte.

* * * * *

UNITED STATES PATENT AND TRADEMARK OFFICE
CERTIFICATE OF CORRECTION

PATENT NO. : 8,860,438 B2  
APPLICATION NO. : 12/777377  
DATED : October 14, 2014  
INVENTOR(S) : Guigen Zhang Page 1 of 1

It is certified that error appears in the above-identified patent and that said Letters Patent is hereby corrected as shown below:

In the Specification:

Column 8, Line 11: Please correct "Angstrom (Ǫ)"
to read -- Angstrom (Å) --

Column 13, Line 48: Please correct "(8) at the electrode"
to read -- (ε) at the electrode --

Signed and Sealed this
Fifth Day of May, 2015

Michelle K. Lee
*Director of the United States Patent and Trademark Office*